April 4, 1939. E. R. ASMUS, SR Plant Pat. 323
ROSE
Filed March 17, 1938
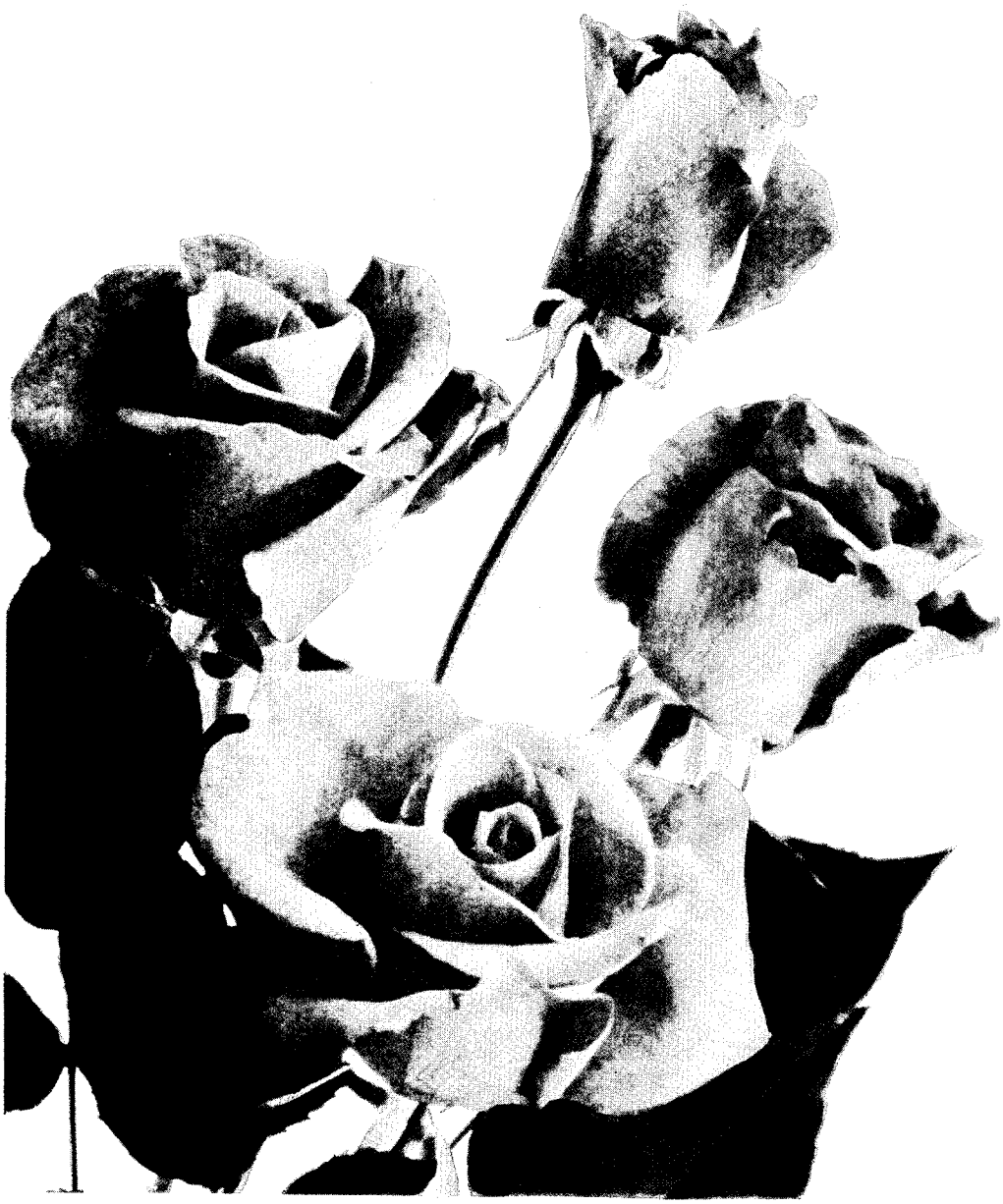
Inventor
Edward Richard Asmus, Sr.
By Robb & Robb
Attorneys Patented Apr. 4, 1939

UNITED STATES PATENT OFFICE

323

ROSE

Edward Richard Asmus, Sr., Closter, N. J.

Application March 17, 1938, Serial No. 196,532

1 Claim. (Cl. 47—61)

This discovery relates to a new and distinct variety of rose plant, originating as a sport of "Better Times," but having a number of characteristics distinguishing it from its parent. These characteristics lend attractiveness to the new rose and primarily reside in the unusual color and form of the bloom.

In order to point out the important distinctions, it is desirable to note by way of comparison with Better Times that as regards the bloom, the petals of the present variety are more fluted, while the edges of the petals on the opening bloom give the effect of moderately fluted crepe paper.

In respect to color, this new rose is pomegranate purple, with velvety appearing inner petals, while "Better Times" is cerise. These features enhance the beauty of the flower.

The foliage, too, is different in that the older foliage is darker green and the young foliage is more reddish. Finally, the bloom very definitely lasts longer than that of "Better Times" and retains its color exceptionally well and long before blueing.

By way of further comparison, the present rose differs from my previous Better Times sport (Plant Patent No. 241) in many respects, namely, in form and color of foliage, in form of sepals, number of thorns, and particularly in form, color and number of petals. One of the main distinguishing features is that the old foliage as well as the new has a decided reddish appearance about it.

Asexual reproduction of this new rose shows that it comes true to form.

The following is a detailed description of my new variety, all color references being in accordance with Ridgway's Color Chart (except where otherwise specified) in connection with specimens cut at Closter, New Jersey, September 26, 1938, at 5 p. m. transmitted on ice to Newark, New York, where the color analysis was made at 4 p. m. on September 27, 1938 while the flowers were in excellent condition:

Parentage:
Sport of "Better Times".

Classification:
*Botanic and commercial.*—Hybrid Tea.

*Flower*

Blooming habit:
Location where observations were made—Closter, N. J., except as to color characteristics.
Recurrent—continuous.

Bud:
*Size.*—Medium.
*Form.*—Long, urn; unaffected by wet or hot weather.
*Color.*—When sepals first divide—Plate 1, Oxblood red. When petals begin to unfurl—Plate 1, Carmine Red flecked with Plate 1, Spectrum Red. When half blown: inside of petals—Between Plate 1, Carmine, and Plate 12, Pomegranate Purple; reverse of petals—Plate 12, Pomegranate Purple.
*Sepals.*—Serrated, curl back.
*Calyx.*—Shape—funnel; size—small, slender; aspect—smooth.
*Peduncle.*—Length—medium; aspect—prickly; color—light green; strength—stiff, erect.
*Opening.*—Bud opens very well; is not affected by adverse conditions.

Bloom:
*Size.*—Large; average size when fully expanded—4½ inches.
*Borne.*—Singly.
*Stems.*—Long, strong.
*Form.*—High center; permanence—retains its form to the end.
*Petalage.*—Double; number of petals under normal conditions—20–25.
*Color.*—Center of flower—Plate 12, Pomegranate Purple; outer petals—Between Plate 1, Carmine, and Plate 12, Pomegranate Purple; base of petals (aiglet)—Plate 12, Rose Red with touch of Plate 4, Empire Yellow; inside of petals—Between Plate 1, Carmine, and Plate 12, Pomegranate Purple; reverse of petals—Plate 12, Pomegranate Purple; general tonality from a distance—Deep Rich Red (Carmine 1).
*Variegations.*—Faint deeper color veining of some petals.
*Discoloration.*—No or negligible discoloration at end of third day.

Petals:
*Texture.*—Thick; not affected by wet or hot weather.
*Appearance.*—Inside — velvety; outside — satiny.
*Form.*—Oval, fluted.
*Arrangement.*—Informal; petaloids in center—many, small.
*Persistence.*—Drop off cleanly.
*Fragrance.*—Moderate. Nature—Tea (average Hybrid Tea scent).
*Lasting quality.*—On the plant and as cut flower, long.

Genital organs:

*Stamens, anthers.*—Medium size, many. Color—Lemon (Gravereaux Chart); arrangement—mixed with petaloids, few tucked in calyx.

*Stamens, filaments (threads).*—Medium length; color—reddish.

*Pollen.*—Lemon (Gravereaux Chart).

*Styles.*—Loosely separated, uneven length; medium length, thin.

*Stigmas.*—Lemon and blood red (Gravereaux Chart).

*Ovaries.*—Some protruding from calyx.

*Plant*

Form:

Bush.

Growth:

Vigorous, upright.

Foliage:

Five leaflets.

*Size.*—Large.

*Quantity.*—Normal.

*Color.*—New foliage: Upper side—Plate 31, Ivy Green in center; edges and midrib, Plate 27, Indian Red; under side—Plate 27, Indian Red with whitish pulverulence. Old foliage: Upper side—Plate 31, Yew Green; under side—Plate 17, light Elm Green; ribs and serrations, Plate 27, Deep Corinthian Red.

*Shape.*—Lanceolate.

*Texture.*—Upper side—leathery; under side—rough; ribs and veins—prominent.

*Edge.*—Serrated.

*Serration.*—Single, medium size.

*Rachis.*—Color—reddish; under side—few prickles.

*Stipules.*—Medium, serrated.

*Disease resistance.*—Resistant

Wood:

(Plant as a whole is a harder wooded variety than "Better Times".)

*New wood.*—Color—Jade Green, Plate XI, with decided splash of Dark Greenish Olive, Plate XXX, whereas in "Better Times" it is Cress Green, Plate XXXI; bark—smooth.

*Old wood.*—Color—Cress Green, Plate XXI, whereas in "Better Times" it is Jade Green, Plate XXXI; bark—smooth.

Thorns:

(Divided into thorns, prickles, and short needles.)

*Thorns.*—Quantity on main stalks and laterals—ordinary but more numerous and smaller than in "Better Times"; form—narrow base, medium length; hooked downward like in "Better Times." Color when young—Hydrangea Red, Plate XXVII, whereas in "Better Times" they are Ocher Red, Plate XXVII. Old—Tawny Olive, Plate XXIX, whereas in "Better Times" they are Pecan Brown, Plate XXVIII. Position—irregular.

*Prickles.*—Quantity: main stalks—none; laterals—few on under side. Color—reddish at base becoming transparent as nearing tip.

*Short Needles.*—Quantity: main stalks—some on peduncle; laterals—many on upper side.

I claim:

A new and distinct variety of rose plant, characterized as to novelty by the fluted form of the petals of its bloom, the color and velvety appearance thereof, and the lasting quality of the bloom before blueing occurs, substantially as shown and described.

EDWARD RICHARD ASMUS, Sr.